United States Patent [19]

Lewis, Jr.

[11] Patent Number: 4,935,008
[45] Date of Patent: Jun. 19, 1990

[54] DOUBLE LUMEN INTRODUCING NEEDLE

[76] Inventor: Ronald L. Lewis, Jr., 75 N. Brookside Rd., Springfield, Pa. 19064

[21] Appl. No.: 221,645

[22] Filed: Jul. 20, 1988

[51] Int. Cl.$^5$ .............................................. A61M 5/00
[52] U.S. Cl. .................................... 604/52; 604/164; 604/272
[58] Field of Search .................. 604/44, 52, 164, 167, 604/264, 272–274; 128/898

[56] References Cited

U.S. PATENT DOCUMENTS

| | | |
|---|---|---|
| 519,635 | 5/1894 | Kregel . |
| 2,564,977 | 8/1951 | Hu . |
| 4,098,275 | 7/1978 | Consalvo . |
| 4,099,528 | 7/1978 | Sorenson et al. . |
| 4,134,402 | 1/1979 | Mahurkar . |
| 4,203,436 | 5/1980 | Grimsrud . |
| 4,403,983 | 9/1983 | Edelman et al. ..................... 604/43 |
| 4,493,696 | 1/1985 | Uldall ................................... 604/43 |
| 4,619,643 | 10/1986 | Bai ....................................... 604/43 |
| 4,626,240 | 12/1986 | Edelman et al. ..................... 604/43 |
| 4,675,004 | 6/1987 | Hadford et al. ...................... 604/44 |
| 4,682,978 | 7/1987 | Martin .................................. 604/43 |

Primary Examiner—Stephen C. Pellegrino
Attorney, Agent, or Firm—Robert A. Koons, Jr.; James Albert Drobile

[57] ABSTRACT

An introducing needle having two lumens is disclosed. The lumens originate at the sharpened end of the needle in a parallel relationship. The first lumen is rectilinear along the entire longitudinal length of the needle and is adapted to engage a syringe barrel at the needle's hub end. The second lumen is rectilinear along the substantial longitudinal length of the needle and diverges from the first lumen at the needle's hub end. In operation, after a blood vessel is punctured by the sharpened end of the needle, a "flash" of blood is drawn through the first lumen and a guidewire is thereafter inserted through the diverging second lumen without disengaging the syringe barrel from the first lumen. In this manner, manipulation of the needle during insertion of the guidewire is substantially reduced, thereby reducing patient discomfort, trauma to the vein, and the possibility of movement of the needle from the initial puncture location.

A method of inserting a guidewire into a blood vessel using an apparatus of the invention is also disclosed.

A method using an apparatus of the invention to insert two guidewires into a blood vessel through the same puncture location is further disclosed.

11 Claims, 2 Drawing Sheets

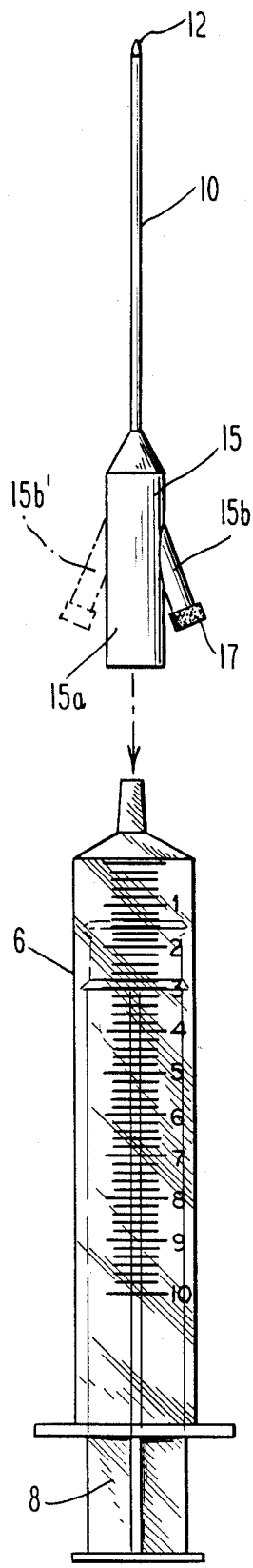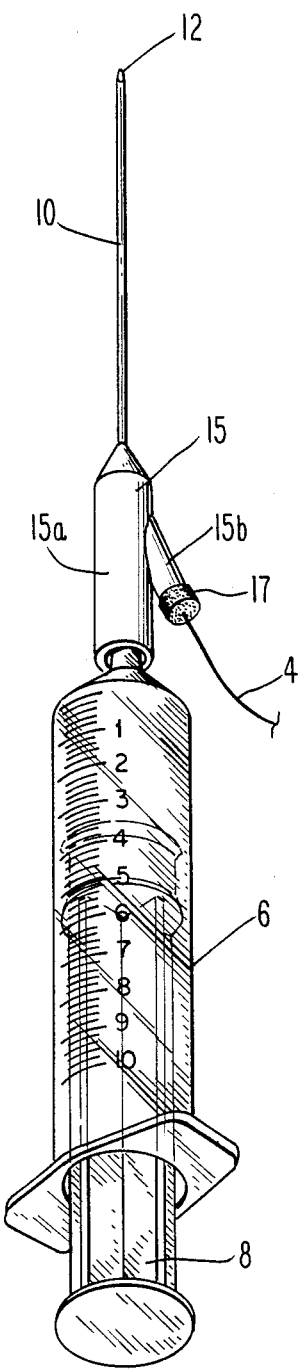
Fig. 2
Fig. 1

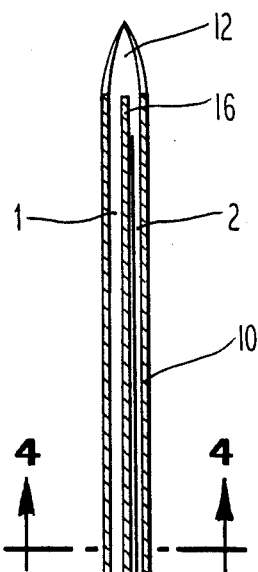
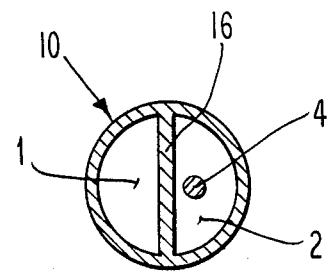
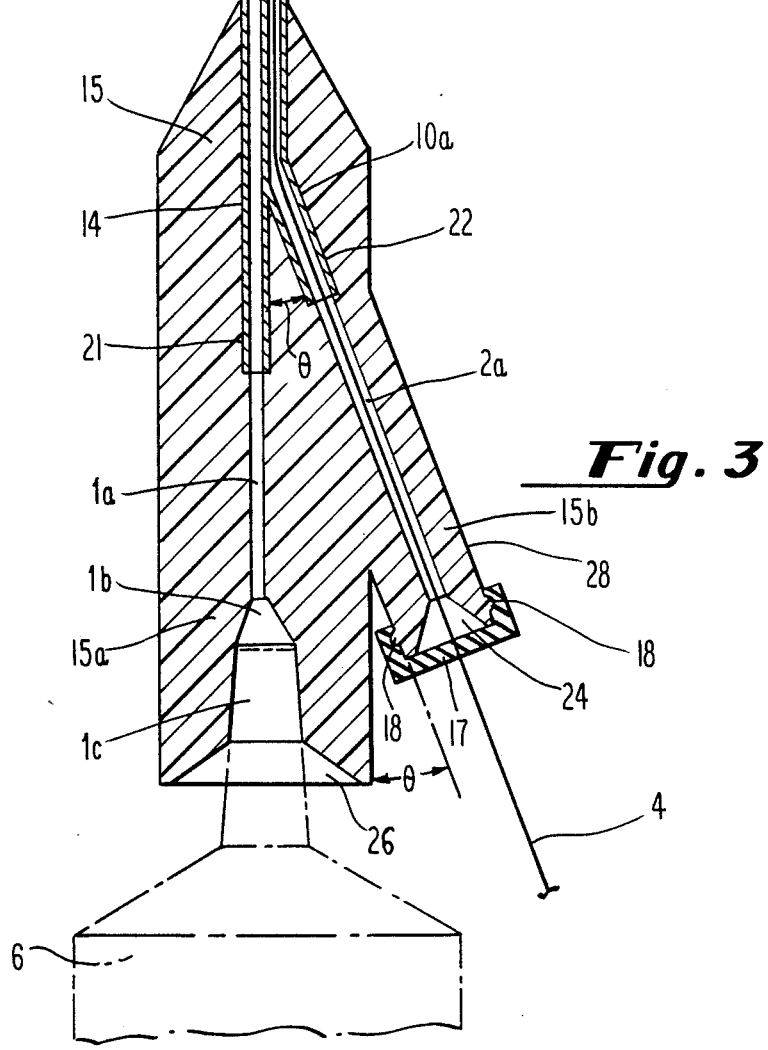
Fig. 3
Fig. 4

DOUBLE LUMEN INTRODUCING NEEDLE

Background of the Invention

The disclosed invention relates to medical needles, and more particularly to introducing needles, i.e., needles used to "introduce" guidewires into human blood vessels during various medical procedures. The invention also relates to a method for introducing guidewires into human blood vessels using the disclosed apparatus of the invention.

In the practice of modern medicine, it often is necessary to insert one or more guidewires directly into human blood vessels. These guidewires may be used as "pilots" for subsequent insertion of various types of catheters, wherein the catheter is concentrically inserted over a guidewire previously inserted into a blood vessel, after which the guidewire is withdrawn, leaving the catheter positioned within the blood vessel. In cardiac medicine, guidewires also may be inserted into a blood vessel and thereafter "worked" through the vessel toward a patient's heart in order to clear blockages or implant permanent cardiac pacemakers, among other things.

Depending upon the particular medical procedure performed, guidewires may be inserted into either veins or arteries, although, in practice, guidewires are most often inserted into veins because of the increased risks in working with pressurized arteries. As a result, the present invention is described in terms of the introduction of guidewires into veins. However, it should be understood that the invention is not limited to use in veins and may, under appropriate circumstances, be used for procedures involving insertion of guidewires into arteries.

Present introducing needles resemble standard "hypodermic" needles in that they have only a single bore or "lumen". The principal difference between introducing needles and hypodermic needles is that the lumen of an introducing needle generally has a larger internal diameter in order to accommodate passage of a guidewire. A guidewire is introduced into a vein using a single lumen needle by first puncturing the vein with the sharpened tip of the needle and thereafter drawing back on the plunger of the syringe barrel attached to the needle so that a "flash" of blood is obtained. This ensures that the vein has been completely punctured and the needle tip is properly positioned within the vein's interior cavity. The syringe barrel then is disengaged and removed from the needle and the guidewire is inserted into the exposed hub of needle and thereafter through the single lumen and into the vein.

Single lumen introducing needles have several disadvantages. As described above, after a vein is punctured with a single lumen needle and a flash of blood is drawn, the syringe barrel must be disengaged and removed from the needle before insertion of the guidewire can be accomplished. The process of disengaging and removing the syringe barrel from the needle necessarily involves pulling, twisting, or turning the syringe barrel in relation to the needle. This may cause substantial manipulation of the needle while it is in place within the vein, which often results in trauma to the vein and unnecessary discomfort to the patient. Moreover, this manipulation of the needle may result in its movement from the initial puncture site, thereby preventing free passage of the guidewire into the vein and requiring that the vein be repunctured, with further increased risks of trauma to the vein and discomfort to the patient.

Another disadvantage of present single lumen introducing needles is that, when performing procedures requiring insertion of two guidewires into a vein, two separate introducing needles must be used, since each needle has only a single lumen that will allow passage of one guidewire through the needle and its puncture location. As a result, when two guidewires are required, it is necessary to insert one guidewire through each of two separate needles that puncture the particular vein at two separate locations. This procedure significantly increases the risk of patient discomfort and trauma to the vein, particularly when the two separate puncture locations are in close proximity to each other.

Objects of the Invention

It is an object of this invention to provide an introducing needle that substantially reduces the amount of manipulation applied to the needle during insertion of a guidewire into a vein punctured by the needle.

It is a further object of this invention to provide a double lumen introducing needle that eliminates the need to disengage and remove the syringe barrel from the needle to accomplish insertion of a guidewire into a vein punctured by the needle.

It is yet a further object of this invention to provide a double lumen introducing needle that enables two guidewires to be inserted into a vein through the single puncture location of the needle.

It is another object of this invention to provide a method for inserting a guidewire into a vein wherein the amount of manipulation applied to the introducing needle during the insertion procedure is substantially reduced.

It is yet another object of this invention to provide a method for inserting a guidewire into a vein without having to disengage and remove the syringe barrel from the introducing needle during the insertion procedure.

It is still another object of this invention to provide a method for inserting two guidewires through a single introducing needle and into a vein at a single puncture location.

These and other objects of the invention will be better appreciated after reading the succeeding description of the invention in conjunction with the accompanying drawings.

Summary of the Invention

The disclosed invention provides an introducing needle having two longitudinal bores or "lumens". The lumens originate in a parallel relationship at the sharpened end of the needle and remain in that relationship along the substantial longitudinal length of the needle. The first lumen is rectilinear along the entire longitudinal length of the needle and terminates at the needle's "hub" end in a configuration suitable for engagement to a standard syringe barrel. The second lumen is rectilinear along the substantial longitudinal length of the needle but diverges from the first lumen at an acute angle at the needle's hub end. The second lumen terminates in a "sidearm" that is capped by a snugly fitting pierceable grommet constructed of rubber or similar material, so that air is prevented from entering the second lumen and the vein punctured by the sharpened end of the needle during insertion of a guidewire.

The disclosed invention also provides a method for inserting a guidewire into a vein using a double lumen needle having a first rectilinear lumen and a second diverging lumen. After a vein is punctured by the sharpened end of the needle, the syringe barrel engaged to the needle's first lumen is drawn back so that a "flash" of blood is obtained, thereby ensuring that the vein has been completely punctured and the sharpened end of the needle is properly positioned within the vein's interior cavity. The doctor performing the particular procedure thereafter securely grasps the needle and syringe barrel in one hand so the needle is maintained in a fixed position with respect to the vein. At the same time, without disengaging and removing the syringe barrel from the first lumen, the doctor uses his other hand to feed the guidewire through the needle's second lumen and into the vein punctured by the needle's sharpened end. In this manner, manipulation of the needle is substantially reduced after the vein is punctured, thereby reducing patient discomfort, trauma to the vein, and the possibility of movement of the needle from the initial puncture location.

The disclosed invention also provides a method for inserting two guidewires into the same vein through a single puncture location. This is accomplished by puncturing a vein with a double lumen needle and inserting a first guidewire into the vein through the second diverging lumen, as described immediately above. Thereafter, the syringe barrel is disengaged and removed from the hub end of the first rectilinear lumen and a second guidewire is inserted through the first lumen and into the interior cavity of the punctured vein. In this manner, the two guidewires are inserted into the vein through the single puncture location of the double lumen needle, thereby avoiding puncturing the vein with two separate single lumen needles at two separate locations. This substantially reduces the risk of patient discomfort and excessive trauma to the vein.

Description of Drawings

1. FIG. 1 is a perspective view of the preferred embodiment of an apparatus of the invention, co-joined with a standard syringe barrel.

2. FIG. 2 is a longitudinal front view of the preferred embodiment of an apparatus of the invention, shown with a detached standard syringe barrel suitable for use with the preferred embodiment.

3. FIG. 3 is a longitudinal front sectional view of the preferred embodiment of an apparatus of the invention.

4. FIG. 4 is a plan sectional view of the preferred embodiment of an apparatus of the invention taken substantially along sectional line 4—4 of FIG. 3.

Detailed Description of the Preferred Embodiment of an Apparatus and Method of the Invention Viewing FIG. 1 in conjunction with FIGS. 2, 3, and 4, it will be seen that the preferred embodiment of an apparatus of the invention comprises generally a needle 10 constructed of stainless steel or similar material and having a sharpened bevelled end 12 and a hub end 14. Needle 10 has a first longitudinal bore or "lumen" 1 and a second longitudinal bore or "lumen" 2. First lumen 1 and second lumen 2 originate at bevelled end 12 of needle 10 in a parallel relationship, with first lumen 1 and second lumen 2 being separated from each other by interior dividing wall 16 of needle 10. First lumen 1 and second lumen 2 are of sufficient internal diameter to allow passage of guidewires commonly used in various medical procedures.

First lumen 1 is rectilinear along the entire longitudinal length of needle 10 and has its terminus 21 at hub end 14 of needle 10. Second lumen 2 is rectilinear along the substantial longitudinal length of needle 10, with terminus 22 of second lumen 2 diverging at an acute angle $\theta$ from first lumen 1 at hub end 14 of needle 10, thereby forming sidearm 10a of needle 10. Angle $\theta$ formed by diverging terminus 22 of second lumen 2 with respect to first lumen 1 generally may be from approximately 10 degrees to approximately 60 degrees, with approximately 10 to approximately 45 degrees being more appropriate, and approximately 20 degrees being preferred.

In the preferred embodiment, hub casing 15 is provided and constructed of plastic or similar material. Hub casing 15 is concentrically attached to needle 10 at hub end 14 and sidearm 10a in a manner known and used for the attachment of hub casings of present single lumen needles. Hub casing primary body 15a is rectilinear and extends from terminus 21 of first lumen 1. Hub casing sidearm 15b extends from terminus 22 of second lumen 2 and diverges from hub casing primary body 15a at the same acute angle $\theta$ at which second lumen 2 diverges from first lumen 1. Hub casing primary body 15a has internal bore 1a which is contiguously aligned with first lumen 1. Hub casing sidearm 15b has internal bore 2a which is contiguously aligned with second lumen 2.

Bore 1a of hub casing primary body 15a increases in diameter at bore expansion 16, with terminus 1c of bore 1a being adapted to removably engage a standard syringe barrel 6 in a manner known and used in present single lumen needles. Bore 1a terminates in an inverted frusto-conically shaped aperture 26 formed into hub casing primary body 15a for the purpose of facilitating the ready insertion of a guidewire into bore 1a and first lumen 1 of needle 10. Similarly, bore 2a terminates in an inverted frusto-conically shaped aperture 24 formed into hub casing sidearm 15b, thereby facilitating the ready insertion of guidewire 4 into bore 2a and second lumen 2 of needle 10, as will be more fully described below.

Bore 2a and hub casing sidearm 15b are sealingly engaged by grommet 17 constructed of rubber or similar material. Grommet 17 is retained by locking bead 18 formed around the exterior surface 28 of hub casing sidearm 15b, as shown in FIG. 3. Grommet 17 is adapted to be pierced and penetrated by guidewire 4, thereby allowing insertion of guidewire 4 through grommet 17 and into bore 2a and second lumen 2 of needle 10 while substantially prohibiting the entry of air into a vein punctured by bevelled end 12 of needle 10.

The method of using an apparatus of the invention will now be described with reference to a right-handed doctor inserting a guidewire into a vein. Viewing FIG. 1 in conjunction with FIGS. 3 and 4, it will be understood that, in preparing to insert guidewire 4 into a vein, an apparatus of the invention is positioned in accordance with accepted medical procedure so that bevelled end 12 of needle 10 faces up, i.e., away from the vein to be punctured. When the apparatus of FIG. 1 is so oriented, hub casing sidearm 15b will be laterally positioned so that hub casing sidearm 15b projects from the right-hand side of hub casing primary body 15a during puncture of the vein. After puncture, piston 8 of syringe barrel 6 is drawn back to obtain a "flash" of blood, thereby ensuring that bevelled end 12 of needle 10 has completely punctured the vein and is properly positioned within its interior cavity.

After the "flash" of blood is drawn, the right-handed doctor grasps syringe barrel 6, hub casing 15, and needle 10 securely in his left hand so that needle 10 is maintained in a fixed position with respect to the punctured vein. At the same time, the right-handed doctor grasps guidewire 4 in his right hand and, after piercing and penetrating grommet 17 with guidewire 4, inserts guidewire 4 through bore 2a of hub casing sidearm 15b and subsequently through second lumen 2 of needle 10 and into the punctured vein. Insertion of guidewire 4 in this method is accomplished without removing syringe barrel 6 from hub casing 15, as presently required with existing single lumen introducing needles. This method substantially reduces manipulation of needle 10 after the vein is punctured, thereby reducing patient discomfort, trauma to the vein, and the possibility of movement of bevelled end 12 of needle 10 from the initial puncture site.

Now viewing more particularly FIG. 2, there is shown the preferred embodiment of an apparatus of the invention suitable for use by a left-handed doctor. In FIG. 2, it will be seen that hub casing sidearm 15b' (shown in broken lines) is provided so that hub casing sidearm 15b' *will extend laterally from the left-hand side of hub casing primary body 15a* when needle 10 is positioned so that bevelled end 12 faces away from the vein being punctured. In this preferred embodiment, hub casing sidearm 15b for use by right-handed doctors would, of course, be eliminated. This preferred embodiment is used by a left-handed doctor in the manner described above for right-handed doctors, except that a left-handed doctor would securely grasp syringe barrel 6, hub casing 15, and needle 10 in his right hand while using his left hand to insert guidewire 4 into bore 2a' (not shown) corresponding to bore 2a and subsequently through lumen 2' (not shown) corresponding to lumen 2 and into the punctured vein.

It will be appreciated that there are considerable variations that can be accomplished in both the apparatus and method of the invention without departing from the invention's scope. As a result, although the preferred embodiment of an apparatus of the invention and a preferred method of the invention have been described above, it is emphasized that the invention is not limited to the preferred embodiment or method, and there exist alternative embodiments and methods that are fully encompassed within the invention's scope, which is intended only to be limited by the scope of the appended claims.

By way of example, it is to be understood that the precise point at which second lumen 2 diverges from first lumen 1 is a matter of design choice and convenience and is not limited by the disclosure of the preferred embodiment. Similarly, the precise locations and configurations of terminus 21 of first lumen 1 within hub casing primary body 15a and terminus 22 of second lumen 2 within hub casing sidearm 15b are matters of convenience and design choice and are not limited in any way by the disclosure of the preferred embodiment. As a result, it will be appreciated that the respective longitudinal lengths and geometric configurations of first lumen 1, second lumen 2, bore 1a and bore 2a may vary within the overall scope of the invention.

By way of further example, although the described method of using the preferred embodiment of the invention involved insertion of only one guidewire into a vein, the invention also can be used to insert two guidewires into the same vein through a single puncture location. Thus, after a first guidewire has been inserted through bore 2a of sidearm 15b and subsequently through second lumen 2 of needle 10 and into a vein as previously described, a second guidewire (not shown) can be inserted into the same vein by disengaging and removing syringe barrel 6 from terminus 1c of bore 1a and thereafter inserting the second guidewire through bore 1a and subsequently through first lumen 1 of needle 10 and into the vein. This method accomplishes the insertion of two guidewires into the same vein through the single puncture site of needle 10, thereby avoiding puncturing the vein with two separate single lumen needles at two separate locations. This substantially reduces the risk of patient discomfort and excessive trauma to the vein.

I claim:

1. An introducing needle for use with a syringe barrel to draw blood and insert guidewires into a blood vessel, comprising:
   a. a needle having a hub end and a bevelled end for puncturing a blood vessel;
   b. said needle having first and second longitudinal lumens originating in a parallel relationship at the bevelled end of said needle;
   c. said first lumen being rectilinear along the entire longitudinal length of said needle and having its terminus at the hub end of said needle;
   d. said second lumen being rectilinear along the substantial longitudinal length of said needle;
   e. said second lumen having its terminus diverging at an acute angle $\theta$ from said first lumen at said hub end of said needle;
   f. a hub casing concentrically attached to said needle;
   g. said hub casing having a rectilinear primary body extending from the terminus of said first lumen of said needle;
   h. said hub casing primary body having an internal bore contiguously aligned with said first lumen of said needle;
   i. said internal bore of said hub casing primary body being adapted to engage a syringe barrel;
   j. said hub casing having a sidearm extending from the terminus of said second lumen of said needle and diverging at said acute angle $\theta$ from said hub casing primary body; and
   k. said hub casing sidearm having an internal bore contiguously aligned with said second lumen of said needle.

2. A needle as set forth in claim 1, further comprising a pierceable grommet adapted to sealingly engage said hub casing sidearm and said internal bore of said hub casing sidearm so that air is substantially prohibited from entering a blood vessel during insertion of a guidewire into a blood vessel punctured by the bevelled end of said needle.

3. A needle as set forth in claim 1 or 2, wherein said internal bore of said hub casing sidearm terminates in an inverted frusto-conically shaped aperture for the purpose of facilitating insertion of a guidewire into said internal bore of said hub casing sidearm and said second lumen of said needle.

4. A needle as set forth in claim 3, wherein said internal bore of said hub casing primary body terminates in an inverted frusto-conically shaped aperture for the purpose of facilitating insertion of a guidewire into said internal bore of said hub casing primary body and said first lumen of said needle.

5. A needle as set forth in claim 4, further comprising a syringe barrel engaged to said internal bore of said hub casing primary body so that blood can be drawn through said internal bore of said hub casing primary body and said first lumen of said needle from a blood vessel punctured by said bevelled end of said needle.

6. A needle as set forth in claim 3, further comprising a syringe barrel engaged to said internal bore of said hub casing primary body so that blood can be drawn through said internal bore of said hub casing primary body and said first lumen of said needle from a blood vessel punctured by said bevelled end of said needle.

7. A needle as set forth in claim 2, further comprising a syringe barrel engaged to said internal bore of said hub casing primary body so that blood can be drawn through said internal bore of said hub casing primary body and said first lumen of said needle from a blood vessel punctured by said bevelled end of said needle.

8. A needle as set forth in claim 1, further comprising a syringe barrel engaged to said internal bore of said hub casing primary body so that blood can be drawn through said internal bore of said hub casing primary body and said first lumen of said needle from a blood vessel punctured by said bevelled end of said needle.

9. A method of introducing a guidewire into a blood vessel, comprising the steps of:
  a. first puncturing a blood vessel with a needle having a bevelled end, a hub end, and a pair of lumens originating in a parallel relationship at the bevelled end of the needle, the first lumen being engaged at the hub end of the needle to a syringe barrel and the second lumen diverging at an acute angle from the first lumen;
  b. next drawing blood through the first lumen of the needle with the syringe barrel to ensure that the bevelled end of the needle has completely punctured the blood vessel and is properly positioned within the blood vessel's interior cavity;
  c. next grasping the needle and syringe barrel in one hand so that the needle and syringe barrel are maintained in a fixed position with respect to the blood vessel;
  d. while grasping the needle and syringe barrel in one hand and maintaining them in a fixed position with respect to the blood vessel, simultaneously using the other hand to insert a guidewire through the second lumen of the needle and into the blood vessel;
  e. after the guidewire has been inserted through the second lumen of the needle and into the blood vessel, withdrawing the needle from the blood vessel over the guidewire so that the guidewire remains positioned within the blood vessel.

10. The method set forth in claim 9, further comprising the initial step of sealingly engaging the diverging second lumen of the needle with a pierceable grommet so that entry of air into the blood vessel during insertion of the guidewire is substantially prohibited.

11. A method of introducing two guidewires into a blood vessel through a single puncture location, comprising the steps of:
  a. first puncturing a blood vessel at a single location with a needle having a bevelled end, a hub end, and a pair of lumens originating in a parallel relationship at the bevelled end of the needle, the first lumen being removably engaged at the hub end of the needle to a syringe barrel and the second lumen diverging at an acute angle from the first lumen;
  b. next drawing blood through the first lumen of the needle with the syringe barrel to ensure that the bevelled end of the needle has completely punctured the blood vessel and is properly positioned within the blood vessel's interior cavity;
  c. next grasping the needle and syringe barrel in one hand so that the needle and syringe barrel are maintained in a fixed position with respect to the blood vessel;
  d. while grasping the needle and syringe barrel in one hand and maintaining them in a fixed position with respect to the blood vessel, simultaneously using the other hand to insert a first guidewire through the second lumen of the needle and into the blood vessel;
  e. after the first guidewire is inserted into the blood vessel, disengaging and removing the syringe barrel from the first lumen at the hub end of the needle;
  f. next inserting a second guidewire into the hub end of the needle, through the first lumen, and into the blood vessel; and
  g. after the first guidewire has been inserted through the second lumen of the needle and into the blood vessel and the second guidewire has been inserted into the hub end of the needle and through the first lumen of the needle and into the blood vessel, withdrawing the needle from the blood vessel over the first and second guidewires so that the guidewires remain positioned within the blood vessel.

* * * * *